United States Patent [19]

Taylor

[11] 4,079,064
[45] Mar. 14, 1978

[54] PRODUCTION OF (1,3-DIOXANE)PROPIONALDEHYDE DERIVATIVES

[75] Inventor: Paul D. Taylor, Clinton, N.J.

[73] Assignee: Celanese Corporation, New York, N.Y.

[21] Appl. No.: 733,169

[22] Filed: Oct. 18, 1976

Related U.S. Application Data

[62] Division of Ser. No. 621,719, Oct. 14, 1975.

[51] Int. Cl.$^2$ ............................................. C07D 319/04
[52] U.S. Cl. ............................... 260/340.7; 260/635 A
[58] Field of Search ..................................... 260/340.7

[56] References Cited

U.S. PATENT DOCUMENTS

| | | | |
|---|---|---|---|
| 2,729,650 | 1/1956 | Habeshaw | 260/340.7 |
| 2,888,492 | 5/1959 | Fischer et al. | 260/635 |
| 3,929,915 | 12/1975 | Cumbo et al. | 260/340.7 X |
| 3,963,754 | 6/1976 | Cumbo et al. | 260/340.7 |
| 4,003,918 | 1/1977 | Hughes | 260/340.7 |
| 4,017,550 | 4/1977 | Kummer | 260/340.7 X |

*Primary Examiner*—Ethel G. Love

[57] ABSTRACT

This invention provides a process for producing 3-(1',3'-dioxane)propionaldehyde or 3-(alkyl-1',3'-dioxane)propionaldehyde in over 70 weight percent yield by the reaction of 2-vinyl-1,3-dioxane or 2-vinyl-alkyl-1,3-dioxane with hydrogen and carbon monoxide under hydroformylating conditions.

2 Claims, No Drawings

PRODUCTION OF (1,3-DIOXANE)PROPIONALDEHYDE DERIVATIVES

This is a division, of application Ser. No. 621,719, filed Oct. 14, 1975 pending.

BACKGROUND OF THE INVENTION

Ethylene glycol is an important constituent of commercial polyester resins. Also of increasing importance as resin constituents are higher polyols such as 1,4-butanediol. The development of new and improved commercial processes for production of higher polyols is under active investigation.

1,4-Butanediol can be derived from tetrahydrofuran, succinic acid, maleic anhydride and other four-carbon organic species, but such methods are not economically attractive. Another method of producing 1,4-butanediol is by the reaction of formaldehyde and acetylene to form 1,4-butynediol as an intermediate, which is subsequently hydrogenated to the desired 1,4-butanediol product.

Other investigators have endeavored to convert acrolein into 1,4-butanediol by subjecting acrolein to hydroformylation conditions, the objective being the formation of succinaldehyde as an intermediate product. The results have been unsatisfactory since the main conversion product recovered from acrolein under hydroformylation conditions is propionaldehyde.

Accordingly, it is an object of the present invention to provide a method for producing 1,4-butanediol.

It is another object of the present invention to provide 3-(alkyl-1',3'-dioxane)propionaldehyde and 3-(alkyl-1',3'-dioxane)propanol as novel classes of compounds.

It is another object of the present invention to provide a novel process for producing 3-(1',3'-dioxane)propionaldehyde and 3-(alkyl-1',3'-dioxane)propionaldehyde.

It is a further object of the present invention to provide 3-(5'-methyl-1',3'-dioxane)propionaldehyde as an intermediate product in a commercially feasible process for converting acrolein into 1,4-butanediol.

Other objects and advantages shall become apparent from the accompanying description and examples.

DESCRIPTION OF THE INVENTION

One or more objects of the present invention are accomplished by the provision of a process which comprises reacting 2-vinyl-1,3-dioxane or 2-vinyl-alkyl-1,3-dioxane with hydrogen and carbon monoxide under hydroformylating conditions to produce 3-(1',3'-dioxane)propionaldehyde or 3-(alkyl-1',3'-dioxane)propionaldehyde:

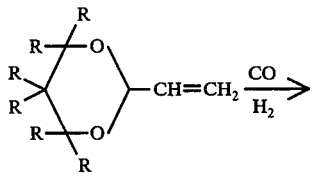

-continued

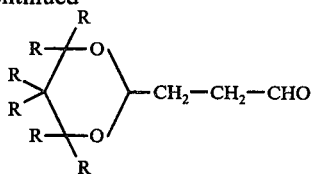

wherein R is hydrogen or an alkyl group containing between one and about five carbon atoms. In the present invention chemical structures, the propionaldehyde moiety is attached to the 2'-position of the 1',3'-dioxane structure, i.e., "acetal" configuration.

The vinyl-1,3-dioxane starting materials as represented in the schematic diagram above can be provided by condensation of acrolein with 1,3-propanediol or alkyl-1,3-propanediol in accordance with conventional procedures:

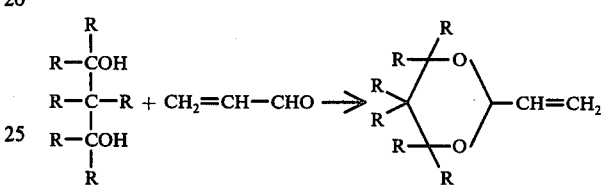

The synthesis of acyclic and cyclic acetals are described in the chemical literature, and in patent literature such as U.S. Pat. Nos. 2,678,950; 2,888,492; 2,915,530; 2,987,524; 3,014,924; and the references cited therein.

Conventional processes for the direct condensation of alpha, beta-unsaturated aldehydes and polyols in the presence of acid catalysts yield large portions of impurities, principally beta-alkoxyacetals and beta-alkoxyaldehydes which are formed by the addition of the polyols across the alpha, beta-double bond of the aldehydes. As a consequence of these undesirable side reactions, attempts have been made to prevent the formation of the aforementioned impurities by reducing the temperature and catalyst concentration; however, these modifications lead to impractically low rates of reaction.

To overcome the disadvantages of conventional processes, U.S. Pat. No. 3,014,924 proposes reacting an alpha, beta-unsaturated aldehyde with an aliphatic polyol bearing at least two hydroxyl groups bonded to different atoms in the polyol molecule in the presence of a catalyst comprising a highly-porous solid carrier having a surface area of at least 75 square meters per gram and about from 0.025 to 1.0 millimole per unit weight of carrier of a strong mineral acid.

One convenient method for preparing the catalysts is to first form a slurry in water or other suitable vehicle of the carrier. Next, an amount of mineral acid sufficient to give the desired weight of acid per unit weight of carrier is added to the slurry. Finally, the water is evaporated, then the catalyst is dried at elevated temperature, for example, at 100° to 150° C. for several hours.

The mineral acids used are, for example, phosphoric acid, hydrobromic acid, hydrochloric acid and sulfuric acid. Orthophosphoric acid is particularly preferred because, in combination with the carrier, it gives a high yield at high rates with a minimum of residue.

Highly-porous silica-alumina gel-type structures such as those prepared essentially by precipitating and calcining an alumina hydrogel with or on a precipitated silica hydrogel are preferred. Other suitable carriers include, for example, silica gel, kieselguhr, diatomaceous earth and porous structures of alumina, silica or various combinations thereof with oxides of zirconium, thorium, chromium and the like. The preferred carriers have some catalytic activity in themselves and, although they are not suitable per se, in combination with the aforementioned mineral acids they give particularly high rates, high yields and a minimum of side reactions.

Preferably, polyol and catalyst are added to a suitable reaction vessel together with a water-immiscible solvent which forms an azeotrope with water and the aldehyde. Next, the alpha, beta-unsaturated aldehyde is added slowly to the reaction mixture. During the reaction, water unreacted aldehyde and azeotroping agent are continuously distilled, the water is separated, then the agent and aldehyde are returned to the reaction vessel. Preferably, the azeotroping agent is at least partially miscible with both reactants. Such preferred agents are, for example, xylene, toluene, benzene, cyclohexane, chloroform, diisobutylene, and hexane.

U.S. Pat. No. 2,888,492 describes a process for producing cyclic acetals which involves reacting an acrolein type aldehyde with a polyol in the presence of 0.02 to 0.06 mole percent based on the amount of ethylenic aldehyde present of a sulfo acid such as sulfuric acid, p-toluene sulfonic acid, ethanesulfonic acid, and the like. The reaction is carried out conveniently by heating a mixture of the chosen alpha, beta-ethylenic aldehyde and polyol, preferably containing about 5 to 50% excess of aldehyde over the stoichiometric requirement for the reaction, dissolved, or suspended in a suitable liquid such as, for instance, benzene, dichloroethylene, and the like. By refluxing at about 50° C. to 90° C. under a phase-separating head until the theoretical amount of water is removed, the reaction is completed in about 1 to 3 hours and high yields of unsaturated cyclic acetals are obtained.

HYDROFORMYLATION CATALYSTS

The present invention process for reacting 2-vinyl-1,3-dioxane or 2-vinyl-alkyl-1,3-dioxane with hydrogen and carbon monoxide under hydroformylation conditions is conducted in the presence of a hydroformylation catalyst.

The preparation of aldehydes and alcohols by the reaction of an olefin with hydrogen and carbon monoxide in the presence of a catalyst is well known in the art, i.e., the "oxo" or "Roelen" reaction. The reaction of an olefin with carbon monoxide and water employing cobalt carbonyl, nickel carbonyl or iron carbonyl is known to produce carboxylic acids (see U.S. Pat. Nos. 2,448,368 and 2,593,440). The reaction of an olefin with carbon monoxide and water produces alcohols when conducted in the presence of an iron carbonyl-tertiary amine complex catalyst [Reppe synthesis; Leibig's Ann. Chem., 582, 133(1953)].

Cobalt catalysts for hydroformylation of olefins to produce alcohols and aldehydes are described in Kirk-Othmer, Encyclopedia of Chemical Technology, 14, 373, 2nd Ed.. Cobalt catalysts are also reviewed in "Catalysis Reviews", 6, 85-131 (1972), published by M. Dekker Inc.

For the purposes of the present invention it has been found that superior results are achieved if the hydroformylation reaction is conducted in the presence of a catalyst which is a complex of a Group VIII metal and a ligand containing phosphorus, arsenic and/or antimony elements. Tertiary amines can also be employed as a ligand in the catalyst complex.

Catalysts which are suitable for the purposes of the present invention hydroformylation process are illustrated by those described in U.S. Pat. Nos. 3,168,553; 3,239,556; 3,239,570; 3,290,379; 3,369,050; 3,420,898; 3,488,296; 3,527,818; 3,725,534; 3,816,337; 3,821,311; 3,825,601; 3,847,997; 3,857,900; 3,859,369; and the like.

For example, any of the metal-phosphine complexes disclosed in "Carbon Monoxide in Organic Synthesis", Falbe, (Springer-Verlag 1970), pages 14-25, may be used. The preferred catalysts are phosphine complexes of rhodium, cobalt, iridium and ruthenium. The most preferred catalysts have the formula $RhCOH(Q_3P)_3$, $RHCOH[(QO)_3P]_3$, $RHCOCl[(QO)_3P]_2$ and $RhCOCl(Q_3P)_2$ wherein Q is phenyl; alkyl phenyl such as tolyl, xylyl, and the like; cyclohexyl; alkyl substituted cyclohexyl such as methyl, propyl, octyl, and the like; substituted cyclohexy; and aliphatic radical such as methyl, butyl, octyl, and the like, or mixtures of any of the foregoing, preferably phenyl. Rhodium catalysts containing tertiary amines are also important hydroformylation catalysts, e.g., a catalyst complex of rhodium metal, carbon monoxide, and a trialkyl amine, triaryl amine or trialkylaryl amine.

A preferred type of rhodium complex catalyst can be characterized by the formula:

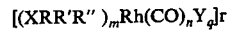

wherein:
 $m$ is 0, 1, 2, 3, or 4;
 $n$ is 0, 1, 2, 3, or 4;
 $q$ is 0, 1, or 3;
 $r$ is 1 or 2;
 Subject to the condition that $m$, $n$, and $q$ are not simultaneously equal to 0.

X represents a phosphorus, arsenic or antimony substituent, said substituent being trivalently bonded to R, R′ and R″ and coordinately bonded to the central rhodium atom;

Y represents a hydrogen substituent, or any of a number of electronegative substituents or substituents which are anionic when in the free state (i.e., substituents which are formally capable of undergoing nucleophilic substitution reactions), e.g., halogen, hydroxyl, alkoxyl, and acylate (i.e., —OOCR‴ wherein R‴ is hydrogen or alkyl) substituents; and R, R′ and R″ each independently represents a substituent selected from the group consisting of aryl substituents of between 6 and about 20 carbon atoms, alkyl substituents of between 1 and 12 carbon atoms, and the corresponding aryloxy, thioaryloxy, alkoxy, thioalkoxy, monoarylamino, monoalkylamino, diarylamino, dialkylamino, and aralkylamino substituents. It is within the scope of the present process that any two of the R, R′ and R″ substituents can constitute a polyalkylene substituent, resulting thereby in phosphine, arsine, or stibine ligands having cyclic structures, e.g.,

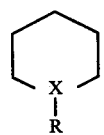 

Referring to the above-described generic formula for the rhodium complex catalyst, it is pointed out that, although the arsine, phosphine, or stibine ligands (XRR'R") are represented in said generic formula as being identical, it is not intended to preclude the possibility that they differ by virtue of independent variation in the nature of the X, R, R', and R" substituents within a given molecule of rhodium complex. For example, when m is 2, 3, or 4, various combinations in the nature of X, R, R', and R" can be employed within the limits of variation established for the substituents hereinabove. An unusual combination of the substituents which is suitable for use in the present process is embodied in the following formula for the rhodium complex, wherein $r=1$, X is a phosphorus substituent, R and R' constitute ethylene substituents bridging two phosphorus atoms, and R' and R" are both phenyl substituents:

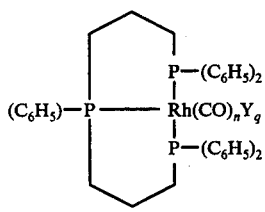

Other variations in the structure of the XRR'R" ligand which are suitable for use in the present invention will suggest themselves to those skilled in the rhodium complex art. An important feature possessed by such XRR'R" ligands when in the free state is low volatility relative to the volatilities of the (1,3-dioxane) aldehyde products. This property of low volatility is desirable in view of the fact that such ligands are capable of being displaced from the rhodium complex by exchange reaction with the free triaryl phosphine, triaryl arsine, or triaryl stibine present in the reaction medium. Another desirable property exhibited by the XRR'R" ligands is thermal stability, i.e., low susceptibility to decomposition at the aforementioned reaction temperatures and pressures.

Preferred rhodium complex catalysts suitable for use in the present process are those whose structures are within the scope of the foregoing generic formula wherein X is a phosphorus substituent R, R' and R" are all phenyl substituents, and Y is a hydrogen, hydroxyl, halogen (especially chlorine), or acylate (especially acetate) substituent. Examples of such preferred rhodium complex catalysts include the following:

1. $Rh(CO)_4H$
2. $(PPh_3)_2Rh(CO)_2H$
3. $(PPh_3)Rh(CO)_3H$
4. $(PPh_3)_3Rh(CO)H$
5. $(PPh_3)_2Rh(CO)Cl$
6. $(PPh_3)_2Rh(CO)OH$
7. $(PPh_3)_2Rh(CO)(OOCCH_3)$
8. $[Rh(CO)_2Cl]_2$
9. $[Rh(CO)_2(OOCCH_3)]_2$
10. $[(PPh_3)_3Rh(CO)]_2$
11. $[(PPh_3)_2Rh(CO)_2]_2$
12. $(PPh_3)_3Rh(OH)$
13. $RhCl_3 \cdot 3H_2O$
14. $Rh(NO_3)_2 \cdot 2H_2O$
15. $(PPh_3)_4RhH$
16. $(PPh_3)_3RhCl_3$
17. $(PPh_3)_3RhCl$ A particularly important aspect of the present invention process is based on the discovery that an exceptionally high yield of straight chain 3-(alkyl-1',3'-dioxane)-propionaldehyde is obtained when the hydroformylation catalyst employed is a complex of rhodium metal, carbon monoxide and triaryl phosphine. Illustrative of this class of catalysts is $$Rh_6(CO)_{16} + Q_3P(\text{excess})$$

It is to be especially noted that "straight chain selectivity" of product yield is promoted when the molar ration of triaryl phosphine ligand to rhodium metal in the hydroformylation reaction medium is at least 10 to 1, and as high as 1000 to 1. Hence, a higher yield of straight chain 3-(alkyl-1',3'-dioxane)propionaldehyde is obtained at the expense of branched chain 2-(alkyl-1',3'-dioxane)propionaldehyde.

HYDROFORMYLATION CONDITIONS

The present invention process for producing 3-(alkyl-1',3'-dioxane)propionaldehyde in high yield selectivity of at least 70 weight percent comprises reacting 2-vinylalkyl-1',3'-dioxane with hydrogen and carbon monoxide in the presence of a hydroformylation catalyst as described hereinabove at a temperature between about 25° C. and 200° C. and a pressure between about 15 and 3000 psi.

Illustrative of a preferred embodiment of the present invention, 3-(5'-methyl-1',3'-dioxane)propionaldehyde is produced in a yield of at least 80 weight percent by reacting 2-vinyl-5-methyl-1,3-dioxane with hydrogen and carbon monoxide in the presence of a metal-ligand complex hydroformylation catalyst at a temperature between 80° C. and 120° C. and a pressure between about 75 and 150 psi. The relative amounts and hydrogen and carbon monoxide employed can vary in accordance with conventional hydroformylation processes, i.e., a molar ratio between 10:1 and 1:10. It has been observed that a high yield of 3-(5'-methyl-1',3'-dioxane)propionaldehyde is favored by increasing the relative ratio of hydrogen to carbon monoxide. Hence, to achieve the conversion of 2-vinyl-5-methyl-1,3-dioxane to 3-(5'-methyl-1',3'-dioxane)propionaldehyde in a yield of 85 weight percent and higher, a molar ratio of 1:1 to 5:1 of hydrogen to carbon monoxide is employed in the presence of a hydroformylation catalyst which is a complex of a Group VIII metal and a ligand containing phosphorus, arsenic and/or antimony elements.

The hydroformylation catalyst is generally employed in a quantity between about 0.001 and 5 weight percent, based on the weight of vinyl(1,3-dioxane) starting material, and preferably a weight percent quantity between about 0.01 and 1.0, exclusive of the weight of ligand if present.

The hydroformylation reaction of the invention may be carried out in a solvent, preferably one which is inert with respect to the products or starting materials, if desired. The solvent generally dissolves the catalyst, starting material and products. It is also possible to use the reaction products as the solvent. The latter is a commonly employed industrial expedient. A wide variety of organic solvents such as, for example, aromatics, aliphatics, esters, ethers, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

If desired, a hydroxylic organic solvent can be provided as a hydroformylation medium. Such solvents are described in U.S. Pat. No. 3,821,311. "Straight chain selectivity" of product yield is enhanced by the use of hydroxylic organic solvents. Illustrative of such solvents are polyhydric alcohols and etherified polyhydric alcohols having at least one unetherified hydroxyl substituent. These solvents are capable of dissolving the starting materials and the hydroformylation catalyst (e.g., rhodium carbonyl and triaryl phosphine complex).

Polyhydric alcohol solvents which are suitable for use in the present process are desirably polyhydric aliphatic alcohols containing between 2 and about 4 hydroxyl substituents and in which the ratio of the number of carbon atoms to the number of hydroxyl substituents per molecule is between 1 and about 2. Examples of such polyhydric aliphatic alcohols include (but are not limited to) ethylene glycol, 1,2-propylene glycol, 1,3-propylene glycol, 2-methyl-1,3-propanediol, 1,3-butylene glycol, 1,4-butanediol, and the like. Etherified polyhydric alcohols suitable for use according to the present invention are desirably derived from aliphatic alcohols and aliphatic polyhydric alcohols, must have at least one unetherified hydroxyl substituent and desirably contain between 2 and about 4 hydroxyl substituents (including etherified and unetherified hydroxyl substituents) per molecule. It is also a desirable feature of these partially etherified aliphatic polyhydric alcohols that the ratio of the number of carbon atoms to the total number of etherified and unetherified hydroxy substituents per molecule is between 1 and about 2. Examples of such partially etherified polyhydric alcohols include (but are not limited to) ethylene glycol monomethyl ether (i.e., HOCH$_2$—CH$_2$OCH$_3$), diethylene glycol (i.e., HOCH$_2$—CH$_2$—O—CH$_2$CH$_2$OH), diethylene glycol monomethyl ether (i.e., HOCH$_2$CH$_2$—O—CH$_2$CH$_2$—OCH$_3$), dipropylene glycol (i.e., HOCH$_2$—CH(CH$_3$)O—CH(CH$_3$)—CH$_2$OH), 3-methyl-1,3-propanediol monomethyl ether, and the like.

For the operation of the present invention hydroformylation process on a large scale, it is advantageous to exclude any solvent from the reaction medium. Excellent results can be achieved, for example, by employing a rhodium carbonyl catalyst component which is incorporated in a large excess of triphenyl phosphine. The said triphenyl phospine can be included in the reaction medium in a quantity which is between 20 and 90 percent of the total weight of catalyst and vinyl (1,3-dioxane) reactant. Triphenyl phosphine at a temperature above about 80° C. is highly fluid and performs as an excellent medium for the invention hydroformylation process.

If desired, the present invention hydroformylation process can be conducted under conditions which are selected to yield an alcohol derivative rather than an aldehyde derivative as the products of the process. Hence, the present invention contemplates a process which comprises (1) reacting 2-vinylalkyl-1,3-dioxane with hydrogen and carbon monoxide in the presence of a metal-ligand complex hydroformylation catalyst at a temperature between about 80° C. and 120° C. and a pressure between about 300 and 3000 psi to form 3-(alkyl-1,3-dioxane)propionaldehyde, and (2) increasing the temperature to above about 150° C. to convert said 3-(alkyl-1',3'-dioxane)propionaldehyde to 3-(alkyl-1',3'-dioxane)propanol.

A preferred class of catalysts for the two-step process for producing 3-(alkyl-1',3'-dioxane)propanol derivatives are cobalt metal hydroformylation catalysts which are phosphine-modified. A suitable catalyst for such a process is a complex of cobalt metal, carbon monoxide and trialkyl phosphine (e.g., tributyl phosphine).

The temperature in the second step of the process is maintained in the range between about 150° C. and 225° C., and preferably at about 190° C. The pressure in the hydroformylation system is maintained in the range between about 300 and 3000 psi, and preferably between about 500 and 1000 psi.

2-vinyl-5-methyl-1,3-dioxane when subjected to the selected hydroformylation conditions described hereinabove for the two-step process yields a mixture of 3-(5'-methyl-1',3'-dioxane)propanol and 2-(5'-methyl-1',3'-dioxane)propanol:

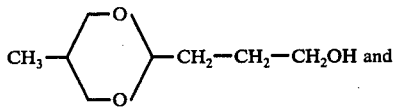

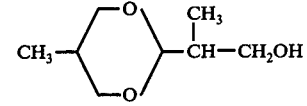

As it is apparent, the two-step hydroformylation process can be moderated to yield a mixture of aldehyde and alcohol deriviates as the product of the process. Also, the two-step process can be operated as a one-step process by maintaining the initial temperature above about 150° C. rather than in the range of 80° C. to 120° C. At elevated temperatures the vinyldioxane starting material is more susceptible to hydrogenation to the corresponding ethyldioxane derivative.

When the present invention hydroformylation procedures were being developed, it was unexpected that 2-vinyl-1,3-dioxane and 2-vinyl-alkyl-1,3-dioxane would convert to (1,3-dioxane)propionaldehyde and 3-(alkyl-1',3'-dioxane)propionaldehyde in exceptionally high yield and high straight chain selectivity. Under hydroformylation conditions, essentially no isomerization of the olefinic double bond occurs, and less than one percent of the vinyldioxane starting material is hydrogenated to the corresponding ethyldioxane derivative. This is contrary to what has been observed with the hydroformylation of other olefin compounds. For example, under hydroformylation conditions hexene-1 undergoes about 8 percent isomerization to hexene-2, and about 6 percent hydrogenation to n-hexane

UTILITY

The present invention hydroformylation process is a convenient and efficient method for producing new and useful compounds such as 3-(1',3'-dioxane)propionaldehyde and 3-(alkyl-1',3'-dioxane)propionaldehyde. Such compounds find utility as solvents and plasticizers and as intermediates for the synthesis of alcohols, carboxylic acids, resins, and the like.

In another embodiment of this invention, the present process represents an intermediate synthesis step in the conversion of acrolein to 1,4-butanediol. For example, a new and efficient method for producing 1,4-butanediol comprises (1) condensing 2-methyl-1,3-propanediol with acrolein to form 2-vinyl-5-methyl-1,3-dioxane, (2) converting the 2-vinyl-5-methyl-1,3-dioxane in accordance with the present invention hydroformylation method to a mixture of 2-(5′methyl-1′,3′-dioxane)propionaldehyde and 3-(5′-methyl-1′,3′-dioxane)-propionaldehyde, and (3) hydrogenating said mixture of propionaldehydes at a pH of about 7 to yield a mixture of 1,4-butanediol and 2-methyl-1,3-propanediol, and (4) separating the components of the diol mixture, and recycling the 2-methyl-1,3-propanediol to the first step of the process.

The following examples are illustrative of specific embodiments of the present invention process. As it is apparent to those skilled in the art, in the light of the foregoing disclosure numerous modifications are possible in the practice of this invention without departing from the scope or concept thereof.

EXAMPLE I

Preparation Of 2-Vinyl-5-methyl-1,3-dioxane

Acrolein (59.5 grams) and 2-methyl-1,3-propanediol (83.8 grams) were added to benzene (100 grams) and p-toluenesulfonic acid (0.0596 gram) in a 500 ml flask equipped with a Dean-Stark trap, condenser, heating mantle and magnetic stirrer.

The mixture was heated at reflux for four hours with continuous removal of the water of reaction. The reaction mixture was cooled, neutralized with calcium oxide, filtered, and distilled to yield 66 grams of 2-vinyl-5-methyl-1,3-dioxane (65 percent yield).

When acrolein is condensed with 1,3-butanediol, the product obtained is 2-vinyl-4-methyl-1,3-dioxane (99 percent yield).

EXAMPLE II

Preparation Of 3-(5′-methyl-1′,3′-dioxane)propionaldehyde

A hydroformylation synthesis was conducted in a 300 ml magnetically stirred autoclave in the following manner.

Benzene (60 grams), triphenylphosphine (30 grams), hexa-rhodium hexadecyl-carbonyl [$Rh_6(CO)_{16}$, 0.20 grams] and 2-vinyl-5-methyl-1,3-dioxane (40 grams) were charged into the autoclave and with stirring heated at 90° C. under a constant pressure of 90 psig carbon monoxide/hydrogen (1:1 mole ratio) for 105 minutes.

The reaction mixture was recovered and analyzed by gas chromatography. Analysis indicated that the reaction mixture contained 3-(5′-methyl-1′,3′-dioxane)propionaldehyde (95 mole percent), 2-(5′-methyl-1′,3′-dioxane)propionaldehyde (4 mole percent) and 2-ethyl-5-methyl-1,3-dioxane (1 mole percent). The overall yield of propionaldehydes was 98 percent.

If a cobalt metal-ligand complex hydroformylation catalyst is employed, an additional step of increasing the temperature to above about 150° C. and the pressure to above about 500 psi yields the corresponding propanol derivatives.

EXAMPLE III

Conversion Of Acrolein To 1,4-Butanediol

Acrolein and 2-methyl-1,3-propanediol were condensed to produce 2-vinyl-5-methyl-1,3-dioxane in accordance with the procedure of Example I.

2-vinyl-5-methyl-1,3-dioxane was hydroformylated in accordance with the procedure of Example II to yield a mixture of 3-(5′-methyl-1′,3′-dioxane)propionaldehyde (95 mole percent) and 2-(5′-methyl-1′,3′-dioxane)propionaldehyde (4 mole percent).

The said mixture of propionaldehydes (19.2 grams), water (29.6 grams) and Raney nickel (1.0 gram) were charged into a stirred autoclave. The reaction medium was heated up to 190° C. over a 45 minute period at a constant hydrogen pressure of 300 psig. After the temperature was maintained at 190° C. for an additional 15 minutes, the autoclave was cooled to room temperature and the reaction product mixture recovered. Gas chromatographic analysis indicated that the product mixture consisted essentially of 1,4-butanediol (43.8 mole percent) and 2-methyl-1,3-propanediol (56.2 mole percent).

What is claimed is:

1. A process for producing 3-(5′-alkyl-1′,3′-dioxane)propanol which comprises (1) reacting 2-vinyl-5-alkyl-1,3-dioxane with hydrogen and carbon monoxide in the presence of a cobalt metal-ligand complex hydroformylation catalyst at a temperature between about 80° C. and 120° C. and a pressure between about 500 and 1000 psi to form 3-(5′-alkyl-1′,3′-dioxane)propionaldehyde, and (2) increasing the temperature to above about 150° C. to convert the said 3-(5′-alkyl-1′,3′-dioxane)propionaldehyde to 3-(5′-alkyl-1′,3′-dioxane)propanol.

2. A process in accordance with claim 1 wherein the starting material is 2-vinyl-5-methyl-1,3-dioxane, and the product of the process is 3-(5′-methyl-1′,3′-dioxane)propanol.

* * * * *